US009433737B2

(12) United States Patent
Graboi (10) Patent No.: US 9,433,737 B2
(45) Date of Patent: Sep. 6, 2016

(54) CUFF PRESSURE MEASUREMENT DEVICE FOR A TRACHEAL TUBE

(71) Applicant: Covidien LP, Mansfield, MA (US)

(72) Inventor: Daniel George Graboi, Encinitas, CA (US)

(73) Assignee: Covidien LP, Mansfield, MA (US)

( * ) Notice: Subject to any disclaimer, the term of this patent is extended or adjusted under 35 U.S.C. 154(b) by 687 days.

(21) Appl. No.: 13/841,038

(22) Filed: Mar. 15, 2013

(65) Prior Publication Data

US 2014/0261442 A1  Sep. 18, 2014

(51) Int. Cl.
| | |
|---|---|
| *A61M 16/04* | (2006.01) |
| *A61M 16/00* | (2006.01) |
| *A61M 16/20* | (2006.01) |
| *A61M 39/22* | (2006.01) |
| *A61M 25/10* | (2013.01) |
| *A61M 39/24* | (2006.01) |
| *A61M 39/26* | (2006.01) |

(52) U.S. Cl.
CPC ........... *A61M 16/044* (2013.01); *A61M 16/04* (2013.01); *A61M 16/0434* (2013.01); *A61M 16/20* (2013.01); *A61M 16/201* (2014.02); *A61M 16/202* (2014.02); *A61M 25/10* (2013.01); *A61M 25/1018* (2013.01); *A61M 25/10184* (2013.11); *A61M 25/10185* (2013.11); *A61M 25/10186* (2013.11); *A61M 2016/0027* (2013.01); *A61M 2205/33* (2013.01); *A61M 2205/3344* (2013.01); *A61M 2205/3569* (2013.01); *A61M 2205/3592* (2013.01); *A61M 2205/502* (2013.01); *A61M 2205/6054* (2013.01); *A61M 2205/6072* (2013.01); *A61M 2205/70* (2013.01); *A61M 2210/1032* (2013.01)

(58) Field of Classification Search
CPC ............. A61M 16/00; A61M 16/003; A61M 2016/0027; A61M 16/04; A61M 16/0402; A61M 16/0409; A61M 25/10; A61M 2025/102; A61M 16/0434–16/0459; A61M 25/1002; A61M 2025/1004; A61M 25/1006; A61M 25/1009; A61M 25/1011; A61M 25/1018; A61M 25/10181; A61M 25/10182; A61M 25/10183; A61M 25/10184; A61M 25/10186; A61M 25/10187; A61M 2025/1015; A61M 25/10185; A61M 2025/1013

See application file for complete search history.

(56) References Cited

U.S. PATENT DOCUMENTS

| | | | |
|---|---|---|---|
| 4,872,483 A * | 10/1989 | Shah ................... | A61M 16/044 128/207.15 |
| 4,924,862 A | 5/1990 | Levinson | |
| 5,004,472 A * | 4/1991 | Wallace ............ | A61M 25/1018 128/205.23 |
| 5,029,591 A * | 7/1991 | Teves .................... | A61B 7/023 128/207.15 |

(Continued)

OTHER PUBLICATIONS

Bosch Sensortec, BMP180 Digital, barometric pressure sensor (2011).

(Continued)

*Primary Examiner* — Justine Yu
*Assistant Examiner* — Tu Vo
(74) *Attorney, Agent, or Firm* — Fletcher Yoder PC (57) ABSTRACT

According to various embodiments, methods and systems for determining pressure in an inflatable cuff of a tracheal tube may employ pressure transducers associated with a cuff inflation line. The pressure transducers may be implemented to provide continuous or intermittent cuff pressure. Also provided are inflation assemblies or other devices that incorporate pressure transducers. The inflation assemblies may be coupled to the tracheal tubes via the inflation line.

10 Claims, 5 Drawing Sheets

(56) References Cited

U.S. PATENT DOCUMENTS

| | | | |
|---|---|---|---|
| 5,218,970 A | 6/1993 | Turnbull et al. | |
| 5,361,753 A * | 11/1994 | Pothmann | A61M 16/044 128/202.22 |
| 5,487,383 A | 1/1996 | Levinson | |
| 5,676,346 A * | 10/1997 | Leinsing | A61M 39/26 251/149.1 |
| 5,752,921 A * | 5/1998 | Orr | A61B 5/085 128/207.15 |
| 7,100,891 B2 * | 9/2006 | Doyle | A61M 39/045 251/149.3 |
| 7,273,053 B2 * | 9/2007 | Zocca | A61M 16/044 128/207.14 |
| 7,404,329 B2 | 7/2008 | Quinn et al. | |
| 7,686,019 B2 | 3/2010 | Weiss et al. | |
| 8,033,176 B2 | 10/2011 | Esnouf | |
| 2009/0107497 A1 | 4/2009 | Stenzler et al. | |
| 2010/0004706 A1 * | 1/2010 | Mokelke | A61M 25/10 607/3 |
| 2010/0078030 A1 * | 4/2010 | Colburn | A61M 16/04 128/207.14 |
| 2010/0163023 A1 * | 7/2010 | Singh | A61M 16/04 128/200.26 |
| 2010/0191054 A1 | 7/2010 | Supiez | |
| 2010/0312132 A1 * | 12/2010 | Wood | A61B 5/085 600/529 |
| 2010/0319702 A1 | 12/2010 | Wood et al. | |
| 2010/0319703 A1 * | 12/2010 | Hayman | A61M 16/04 128/207.15 |
| 2010/0326446 A1 * | 12/2010 | Behlmaier | A61M 16/0459 128/207.15 |
| 2011/0046494 A1 * | 2/2011 | Balji | A61B 5/022 600/499 |
| 2011/0092967 A1 * | 4/2011 | Harvey-Poncelet | A61B 18/02 606/21 |
| 2011/0109458 A1 * | 5/2011 | Shipman | A61M 16/044 340/573.1 |
| 2011/0178419 A1 * | 7/2011 | Wood | A61B 5/08 600/529 |
| 2012/0188084 A1 * | 7/2012 | Shipman | A61M 16/044 340/573.1 |

OTHER PUBLICATIONS

The Mini Hybrid from Colder, Colder Products Company, www.colder.com, (2011).

Quiet Operation High Density Interface (HDI) 3-Way Solenoid Valve, Lee Innovation in Miniature, The Lee Company, www.TheLeeCo.com, (2011).

Medical Check Valves, Bespak, p. 4 (2011).

Luer Connector Images/Information (From Industrial Specialties Mfg., Englewook, Co) pp. 5, 8 (2011).

Erikson, J.R., "Connectors Take on a New Life" (2012).

Issue 36: Tubing misconnections—a persistent and potentially deadly occurrence | Joint Commission (2006) http://www.jointcommission.org/SentinelEvents/SentinelEventAlert/sea_36.htm?print=yes[Sep. 20, 2010 11:52:38 AM].

* cited by examiner

CUFF PRESSURE MEASUREMENT DEVICE FOR A TRACHEAL TUBE

BACKGROUND

The present disclosure relates generally to medical devices and, more particularly, to pressure measurement for airway devices, such as tracheal tubes, that include inflatable cuffs.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea and into the lungs, for example during patient ventilation. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

To seal these types of tracheal tubes, an inflatable cuff may be associated with the tubes. When inflated, the cuff generally expands into the surrounding trachea (or, in the case of laryngeal masks, over the trachea) to seal the tracheal passage around the tube to facilitate the controlled delivery of gases via a medical device (e.g., through the tube). As many patients are intubated for several days, healthcare workers may need to balance achieving a high-quality tracheal seal with possible patient discomfort. For example, if improperly overinflated, the pressure and/or frictional force of certain types of inflated cuffs against the tracheal walls may result in some tracheal tissue damage. While a cuff may be inflated at lower pressure to avoid such damage, this may lower the quality of the cuff's seal against the trachea. Low cuff inflation pressures may also be associated with allowing folds to form in the walls of the cuff that may serve as leak paths for air as well as microbe-laden secretions.

A cuff may be inflated manually by the caregiver after intubation, e.g., via an inflation syringe coupled to an inflation line open to an interior of the cuff. The inflation line typically is formed in part within or adjacent to the tracheal tube and extends outward from the tracheal tube as a separate lumen that is then handled by the caregiver. The inflation line also may include features that close fluid access to the inflation line once the syringe is removed to prevent loss of air within the cuff.

SUMMARY

This disclosure provides a novel cuff pressure monitoring and/or cuff inflation device designed to reduce loss of connection and associated changes in cuff pressure. In accordance with a first aspect, a tracheal tube system includes a conduit configured to be inserted into a trachea of a subject; an inflatable cuff disposed on the conduit and configured to contact the trachea of the subject; an inflation line in fluid communication with the inflatable cuff comprising an exterior portion extending away from a wall of the conduit and a distal opening disposed in an interior space of the inflatable cuff. The system also includes an inflation assembly reversibly coupled to a proximal terminus of the exterior portion of the inflation line, the inflation assembly comprising: a pressure sensor in fluid communication with the inflation line; a lumen in selective communication with the inflation line and coupled to a valve configured to control passage of fluids into and out of the inflation line; and a hybrid connector disposed on a proximal terminus of the lumen configured to carry fluid and electrical signals, wherein the valve is closed when the hybrid connector does not carry an electrical signal.

In accordance with another aspect of the disclosure, an inflation assembly includes a fluid passage comprising: a connector configured to be coupled to an inflation line of tracheal tube; a first branch comprising a terminus closed to fluid flow; and a second branch comprising a valve configured to control passage of fluids into and out of the inflation assembly. The inflation assembly also includes a pressure sensor in fluid communication with and configured to measure pressure within the inflation assembly; and an electrical connector extending from the terminus of the first branch and coupled to the pressure sensor.

In accordance with another aspect of the disclosure, a measurement assembly includes a fluid connector configured to be coupled to an inflation line of tracheal tube; an electrical connector disposed on a terminus of the inflation assembly, wherein the electrical connector is closed to fluid flow from the terminus; and a pressure sensor in fluid communication with the inflation line with the connector is coupled and configured to measure pressure within the inflation assembly, wherein the pressure sensor is disposed within or adjacent to the electrical connector.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A tracheal tube may be used to seal a patient's airway and provide positive pressure to the lungs when properly inserted into a patient's trachea. A high quality seal of a cuff against the tracheal walls may assist in isolating the lower airway and anchoring the tube in place. However, a conforming seal is often difficult to obtain over long-term intubation. Physicians may attempt to determine the quality of a cuff seal by monitoring inflation pressure via devices such as manometers that are temporarily attached to the exposed valve of the cuff inflation line. However, these devices are generally used intermittently for spot checks of cuff pressure and, therefore, add to the workflow of clinicians. Further, the devices include connecting tubes to transfer gas from the cuff inflation line to pressure sensors. When the devices are disconnected, the air transferred to the devices is lost to the system. Accordingly, each measurement results in an overall decrease in cuff pressure, which may influence the integrity of the cuff seal.

Additionally, these devices may have coupling that, when disconnected, may allow air to flow into or out of the cuff. Certain devices have connecting tubing with two ends, where one end couples to the inflation line via insertion into and opening of the valve that controls air flow into the cuff. The other end of the tubing terminates in a connector that couples to a handheld display or other devices. Depending on the type of connection to the handheld display, a loss of this end coupling may result in an open connection from the exposed end of the connective tubing when its other end remains connected to the inflation line. Even when the coupling is mediated by a locking Luer-type connector on one side, if the female connector is a slip Luer connector, the resulting connection is a less secure slip connection. Further, many of these types of connections are barb or slip connections. Such devices may also rely on operator experience for proper completion of the disconnection process. For example, disconnecting the wrong end leaves the inflation line open to the ambient environment. For devices that are frequently connected and disconnected, each event carries the risk of the operator not being properly trained in device removal.

The disclosed embodiments provide a method and system for determining trachea pressure by obtaining a measurement of pressure with pressure transducers associated with the cuff inflation line or inflation assemblies that couple to the cuff inflation line. The inflation assemblies including integral pressure transducers and may be removable or permanently associated with the inflation line. In particular embodiments, the pressure transducer may be part of an inflation assembly that couples to a proximal-most end of the inflation line, for example via a female slip Luer connection. In one embodiment, an inflation line and pilot balloon assembly may typically terminate at a proximal end in a valve that opens to allow air to enter or leave the inflation line and that is configured to couple to an inflation assembly. Such an embodiment may provide manufacturing advantages because the tracheal tube, inflation line, and pilot balloon are unchanged, and the inflation or cuff measurement assembly, for example, may be provided as an adapter. In additional embodiments, the inflation assembly may terminate in an electrical connector that is coupled to a pressure transducer. In such embodiments, accidental disconnection of the electrical connector will not result in any loss of air from the inflation system, because the electrical connector is closed to air flow. In other embodiments, the electrical connector may be configured such that disconnection automatically closes a valve. Accordingly, an operator cannot disconnect any portion of the assembly in a manner that leaves the inflation line and cuff open to the ambient environment.

In certain embodiments, the disclosed tracheal tubes, systems, and methods may be used in conjunction with any appropriate medical device, including a tracheal tube, an endotracheal tube, a tracheostomy tube, a double-lumen tracheal tube (e.g., an endobroncheal tube), a circuit, an airway accessory, a connector, an adapter, a filter, and/or a humidifier. The present techniques may also be used to monitor cuff pressure in medical devices used for patient ventilation, e.g., positive pressure ventilation.

Figure 1:
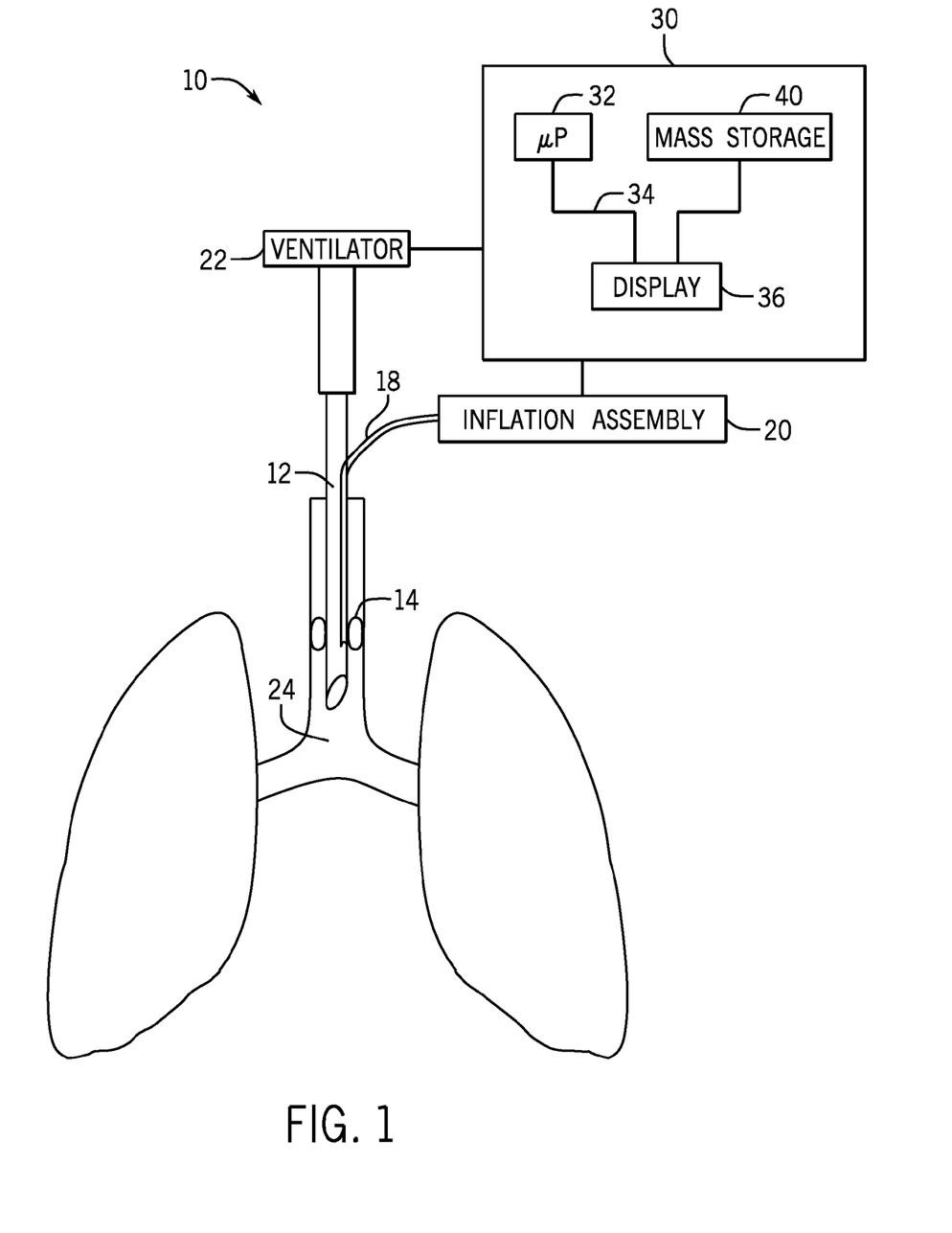
FIG. 1 illustrates a system including a tracheal tube with an inflation assembly with the inflation line for monitoring cuff pressure according to embodiments of the present techniques.

FIG. 1 shows an exemplary tracheal tube system 10 that has been inserted into the trachea of a patient. The system 10 includes a tracheal tube 12, shown here as an endotracheal tube, with an inflatable balloon cuff 14 that may be inflated via inflation line 18 to form a seal against the tracheal walls. The tracheal tube 12 may also include an inflation assembly 20 (or, alternatively, a pressure measurement assembly) that is in fluid communication with the cuff 14. In certain embodiments, the inflation assembly 20 may be coupled to a medical device, such as a ventilator 22 or a monitor 30. The monitor 30 and/or the ventilator 22 may be configured to monitor pressure in the cuff 14 and, in particular embodiments, the pressure in the tracheal space 24 via a pressure transducer associated with the inflation assembly 20.

The system 10 may also include devices that facilitate positive pressure ventilation of a patient, such as the ventilator 22, which may include any ventilator, such as those available from Nellcor Puritan Bennett LLC. The system may also include a monitor 30 that may be configured to implement embodiments of the present disclosure to determine pressures based upon the pressure in the cuff 14. It should be understood that the monitor 30 may be a standalone device or may, in embodiments, be integrated into a single device with, for example, the ventilator 22.

The monitor 30 may include processing circuitry, such as a microprocessor 32 coupled to an internal bus 34 and a display 36. In an embodiment, the monitor 30 may be configured to communicate with the inflation assembly 20, for example via an electrical connector pressure or via an associated antenna, to obtain signals from a pressure transducer. In certain embodiments, the communication may also provide calibration information for the tube 12. The information may then be stored in mass storage device 40, such as RAM, PROM, optical storage devices, flash memory devices, hardware storage devices, magnetic storage devices, or any suitable computer-readable storage medium. The information may be accessed and operated upon according to microprocessor 32 instructions and stored executable instructions. In certain embodiments, calibration information may be used in calculations for estimating of pressure in the cuff based on measurements of pressure in the inflation line or associated structures (e.g., the pilot balloon assembly). The monitor 30 may be configured to provide indications of the cuff pressure, such as an audio, visual or other indication, or may be configured to communicate the estimated cuff pressure to another device, such as the ventilator 22.

Figure 2:
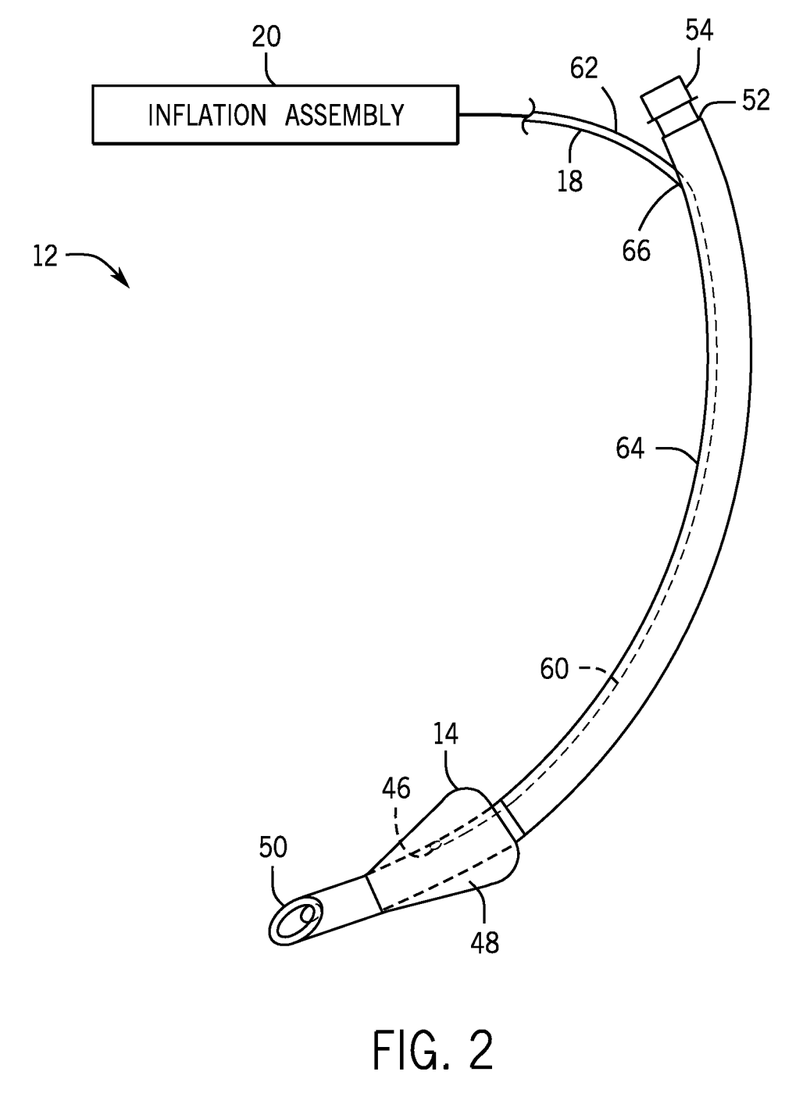
FIG. 2 is a perspective view of an endotracheal tube including an inflation assembly that may be used in conjunction with the system of FIG. 1.

FIG. 2 is a perspective view of an exemplary tracheal tube 12 according to certain presently contemplated embodiments. It should be understood that the embodiments discussed herein may be implemented with any suitable airway device including a cuff 14, such as a tracheal tube, an endotracheal tube, a tracheostomy tube, a laryngeal mask, etc. Further, the embodiments disclosed herein may be used with any medical device that includes an inflatable component that is inflated via an inflation line. For example, the tube 12 includes a cuff 14 inflated via inflation lumen 18, which terminates in an opening 46 that is located within the inflated interior space 48 of the cuff 14. The tracheal tube 14 is inserted in the patient such that the distal end 50 and the cuff 14 are positioned within the trachea (see FIG. 1) and the proximal end 52 is located outside of the patient for connection via connector 54 to a ventilator. The inflation lumen 18 includes an interior portion 60 and an exterior portion 62 that extends away from the wall 64 of the tube 12 at an opening 66.

The tube 12 and the cuff 14 are formed from materials having suitable mechanical properties (such as puncture resistance, pin hole resistance, tensile strength), chemical properties (such as biocompatibility). In one embodiment, the walls of the cuff 14 are made of a polyurethane having suitable mechanical and chemical properties. An example of a suitable polyurethane is Dow Pellethane® 2363-80A. In another embodiment, the walls of the cuff 14 are made of a suitable polyvinyl chloride (PVC). In certain embodiments, the cuff 14 may be generally sized and shaped as a high volume, low pressure cuff that may be designed to be inflated to pressures between about 15 cm $H_2O$ and 30 cm $H_2O$. However, it should be understood that the intracuff pressure may be dynamic. Accordingly, the initial inflation pressure of the cuff 14 may change over time or may change with changes in the seal quality or the position of the cuff 14 within the trachea.

The system 10 may also include a respiratory circuit (not shown) connected to the endotracheal tube 12 that allows one-way flow of expired gases away from the patient and one-way flow of inspired gases towards the patient. The respiratory circuit, including the tube 12, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

The inflation assembly 20 is associated with the inflation lumen 18, either coupled to an end of the inflation lumen 18 or extending from a structure in fluid communication with the inflation lumen 18. In certain embodiments, the inflation assembly is permanently coupled to the inflation lumen, e.g., cannot be removed by a tugging force from an operator. In other embodiments, the inflation assembly 20 is reversibly coupled to an end connector on the inflation lumen 18 and may be removed by an operator with a tugging force.

Figure 3:
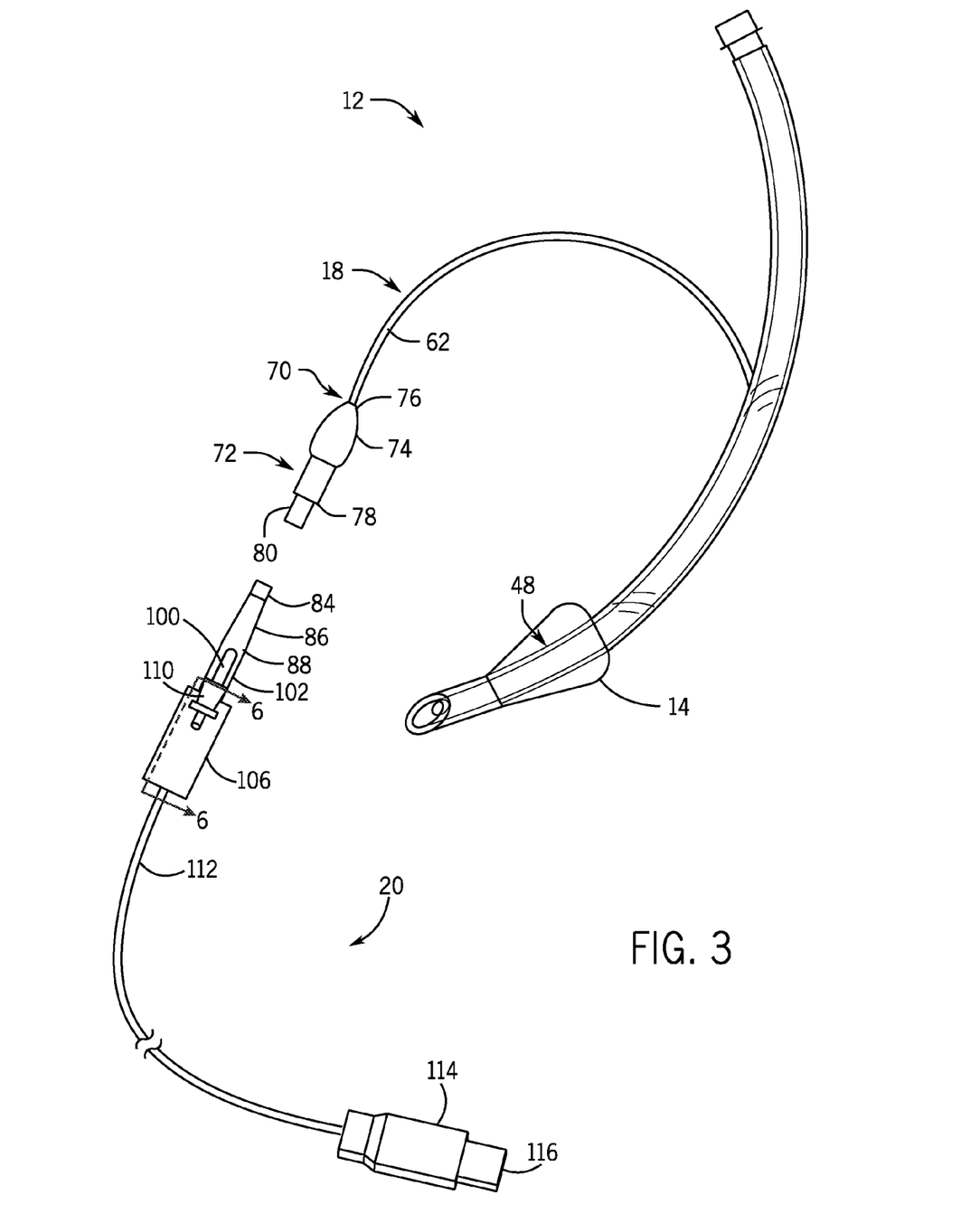
FIG. 3 is a perspective view of an endotracheal tube with a removable inflation assembly including a pressure transducer that may be used in conjunction with the system of FIG. 1.

FIG. 3 illustrates an example of an inflation assembly 20 that couples to an inflation line 18 end connector that may be used to manually inflate the cuff 14. The inflation line 18 terminates at its proximal end 70 in a pilot balloon assembly 72. The inflation assembly 20 may be inserted into the pilot balloon assembly 72, which in the depicted example includes a pilot balloon 74 configured to be in fluid communication with the interior space 48 of the cuff 14. In the depicted embodiment, the proximal pilot balloon end 78 is coupled to a valve connector 80. The valve connector 80 is configured to open to allow the transfer of fluid in or out of the inflation system to inflate or deflate the cuff 14. For example, the valve connector 80 may be a Bespak valve configured to accommodate an inflation syringe. In one implementation, insertion of the syringe may depress a spring-loaded plunger, which opens the valve housed in the valve connector 80. Removal of the syringe allows the plunger to return to a closed configuration of the valve. It should be understood that other configurations of a valve may also be incorporated into the pilot balloon assembly 72.

In the depicted embodiment, the inflation assembly 20 includes a distal connector 84 configured to mate in a complementary manner with the valve connector 80. In one embodiment, the valve connector 80 is a female Luer connector and the distal connector 84 on the inflation assembly is a male Luer connector. The distal connector 84, when inserted, opens the valve in the valve connector 80 and couples a fluid passage 86 of the inflation assembly 20 to the inflation lumen 18. The fluid passage 86 is depicted as a branched passage that includes a main stem 88, a first branch 100, and a second branch 102. Upon insertion, fluid from the inflation lumen 18 is permitted to equilibrate within the fluid passage 86 to reach a pressure sensor 106 associated with the second branch 102. The first branch 100 terminates in a valve connector 110 that is compatible with a syringe to facilitate manual inflation when the inflation assembly 20 is in place. For example, if the valve connector 80 is a female Luer connector, the valve connector 110 is also a female Luer connector. In this manner, the valve connector 110 takes the place of the valve connector 80 when the valve connector 80 holds the inflation assembly 20. The second branch 102 is in fluid communication with the pressure sensor 106, which in turn is in electrical communication with a cable 112 that extends away from the pressure sensor 106 and that terminates in an electrical connector 114 that includes electrical contacts 116 that are configured to mate with a complementary connector. In the embodiments of the inflation assembly 20 disclosed herein, the positions of the first branch 100 and the second branch 102 may be exchanged and the lengths of each and their angle relative to one another may be selected to facilitate operator insertion and removal of the inflation assembly 20 and/or an inflation syringe. It should also be understood that, while the disclosed embodiments may show a branching configuration, the inflation assembly 20 may also include other arrangements of the fluid passage 86, such as a single fluid passage. Further, in certain embodiments, the inflation assembly 20 may include no valve for manual insertion of a syringe. Because, in particular embodiments, the electrical connector 114 is not compatible with a syringe and does not have a female Luer connector and/or a Bespak valve, the disclosed implementations may reduce the possibility of confusion with other functional lumens (e.g., suction lumens) that include such structures.

Figure 4:
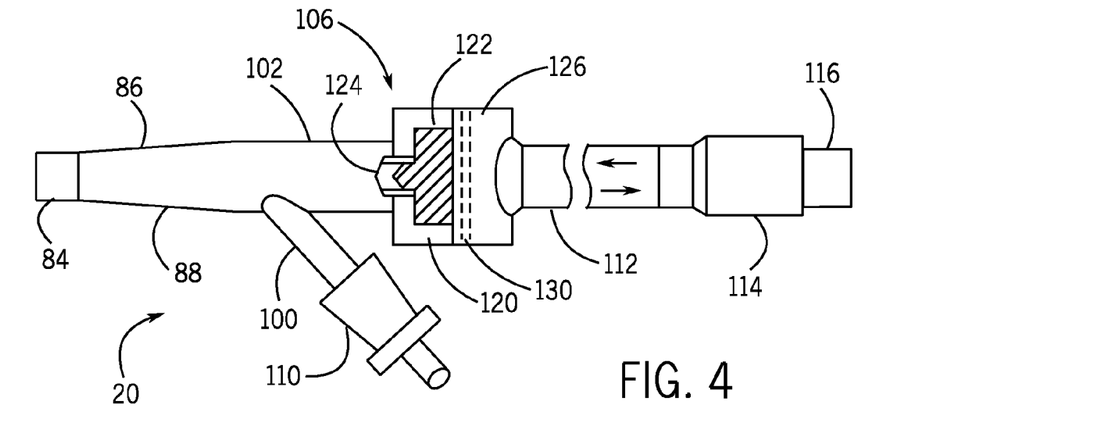
FIG. 4 is a partial cutaway view of an example of the inflation assembly of FIG. 3 along line 6-6.

FIG. 4 is a cutaway view of the inflation assembly 20 of FIG. 3. As illustrated, the second branch 102 terminates at the pressure sensor 106, which may be assembled as a housing 120 holding a pressure transducer 122. In the depicted embodiment, the housing 120 includes a passage 124 that allows air from inside the fluid passage to enter the pressure transducer 122. The inflation assembly 20 is closed at the ends of the first branch 100 and the second branch 102 to fluid entry, with the exception of cases when a syringe or other device enters valve connector 110 and opens the valve. While the pressure sensor 106 may include electrical connectors 126 that couple to leads within the cable 112, the interface 130 with the cable 112 is not open to air flow. In this manner, the fluid from the inflation lumen 18 lost to the pressure sensor 106 may be reduced. Further, the cable length and configuration of the electrical connector 114 and contacts 116 may be implemented without consideration of the relationship between cable length and sensor equilibration time.

In contrast to devices that have an open end, the inflation assembly 20 may be removed or inserted into the inflation lumen 18 without concern for opening the inflation lumen 18 to the ambient environment and subsequent loss of cuff pressure. That is, in contrast to device in which disconnection of couplings in the wrong order may leave the valve connector 80 open to the ambient environment, operation of the inflation assembly 20 as provided reduces the possibility of confusion by simplifying the connection and removal process. Removal of the electrical connector 114 from the monitor 30 has no effect on fluid entry or exit from the inflation assembly 20. Further, removal of the inflation assembly from the valve connector 80 results in closing of the valve and the inflation lumen 18.

The pressure sensor 106 as implemented in conjunction with any of the disclosed embodiments may be any suitable pressure sensor, such as a piezoelectric pressure sensor. In one embodiment, the pressure sensor 106 may incorporate a passive or active RFID circuit that may be read wirelessly to convey pressure monitoring information and/or calibration or identification information to the monitor 30. In particular embodiments, a passive RFID component without power connections or battery components may be advantageous. The monitor 30 may incorporate an RFID readout device. In one embodiment, the pressure sensor 106 may be part of an assembly that includes a capacitor type pressure sensor and a tuned antenna for a resonance frequency in a medical band, such as a frequency in the 2.450 GHz center frequency or the 5.800 GHz band (or higher). The sensor may be a CMUT (capacitive micromachined ultrasonic transducer) sensor with a movable membrane fabricated onto a silicon chip of a size suitable for the embodiments discussed herein. In certain embodiments, a sweep of the transmission frequency measures the resonant frequency of the pressure sensor 106, which is a function of the cuff pressure. The pressure sensor 106 may be capable of sensing pressures in a range of 0 to 50 cm of $H_2O$.

The pressure sensor 106 may also be associated with an information element, such as a memory circuit, such as an EPROM, EEPROM, coded resistor, or flash memory device for storing calibration information for the pressure sensor 106. In certain embodiments, the memory circuit may be contained within the electrical connector 114. The pressure sensor 106 may also be part of an assembly that contains certain processing circuitry for at least partially processing signals from the pressure sensor 106 or for interacting with any memory circuitry provided. When the pressure sensor 106 communicates with the monitor 30, the information element may be accessed to provide calibration information to the monitor 30. In certain embodiments, the calibration information may be provided in a barcode that may be scanned by a reader coupled to the monitor 30. Alternatively, the pressure sensor 106 may include a passive or active RFID circuit that may be read wirelessly to convey pressure monitoring information and cuff calibration information to the monitor 30. For example, in embodiments in which an electrical connector 114 is used in conjunction with a wireless pressure sensor 106, the connector 114 may control other components of the inflation assembly, such as one or more valves.

The electrical connector 114 may be any suitable size and shape for connection to a compatible device, such as the monitor 30 and may include standard connectors developed according to a standards organization, such as the Electronic Industries Alliance. In one embodiment, the electrical connector 114 may be a universal serial bus connector or a USB connector. In other embodiments, the electrical connector 114 may be a proprietary connector associated with a certain type of device (e.g., a brand of smart phone), a binding post connector, a plug and socket connector, a registered jack connector, a pin connector, and/or a blade connector. Further, the connector may include a D-subminiature connector, a mini USB connector, or an AC power connector. Further, the electrical connector may include additional features to prevent coupling to an incompatible medical device. For example, the electrical connector may be configured such that operation of the pressure sensor 106 involves handshake recognition between the monitor 30 and the electrical connector 114. The electrical connector 114 may also allow the monitor 30 to power the pressure sensor 106.

Figure 5:
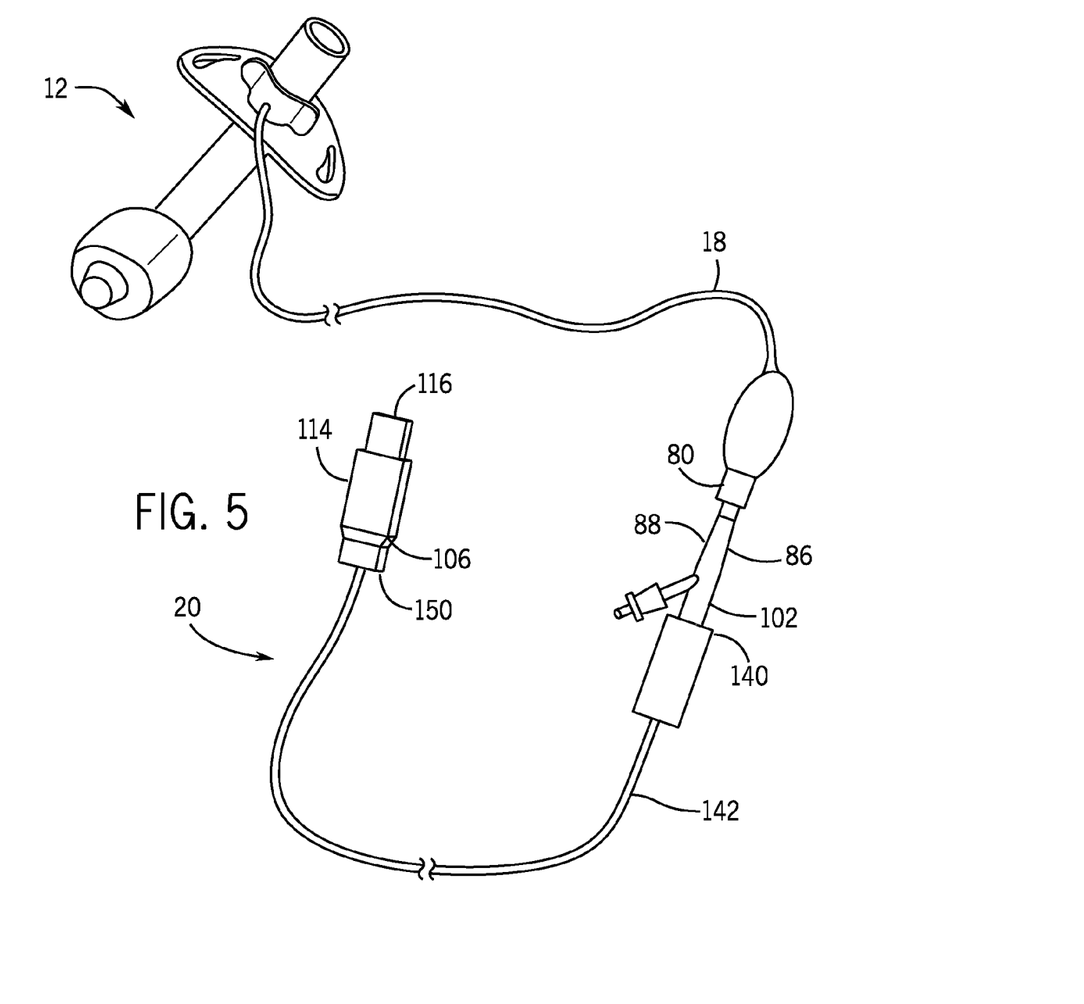
FIG. 5 is a perspective view of an inflation assembly coupled to an end of the inflation line of a tracheostomy tube.

In an alternative implementation, the pressure sensor 106 may be housed within or adjacent to the electrical connector 114. Such an embodiment may be advantageous in reducing crosstalk with other patient-associated sensors. That is, in the depicted embodiment, the entire pressure sensor 106 and associated leads and connectors may be arranged to be away from the patient, which reduces the exposure of other devices to cross talk from signals carried a cable. For example, as illustrated in FIG. 5, the inflation assembly 20 includes a fluid passage 86 coupled to the valve connector 80 of a tracheostomy tube 12, which permits fluid within the inflation lumen 18 to equilibrate within the inflation assembly 20. Rather than terminating fluid flow at a pressure sensor 106 disposed on the end of second branch 102, the second branch 102 includes a coupler 140 that connects the second branch 102 to a lumen 142 that transfers fluid to the pressure sensor 106 coupled to the electrical connector 114. Connection of the electrical connector 114 at the electrical contacts 116 allows the monitor 30 to receive the pressure information. However, because the inflation assembly 20 has a closed end at the electrical connector 114 (i.e., because fluid flow terminates within the pressure sensor 106 and cannot enter via the electrical contact side of the electrical connector 114), inadvertent disconnection of the electrical connector 114 from the monitor 30 has no effect on the fluid levels within the inflation assembly 20 and/or the inflation lumen 18. It is envisioned that the lumen 142 is permanently coupled to the fluid passage 86 at the coupler 140 and to the electrical connector at coupler 150, e.g., via an adhesive or via integral molding. Accordingly, the lumen 142 cannot be inadvertently uncoupled to open the inflation assembly 20 to the ambient environment when the inflation assembly 20 is inserted within the valve connector 80.

Figure 6:
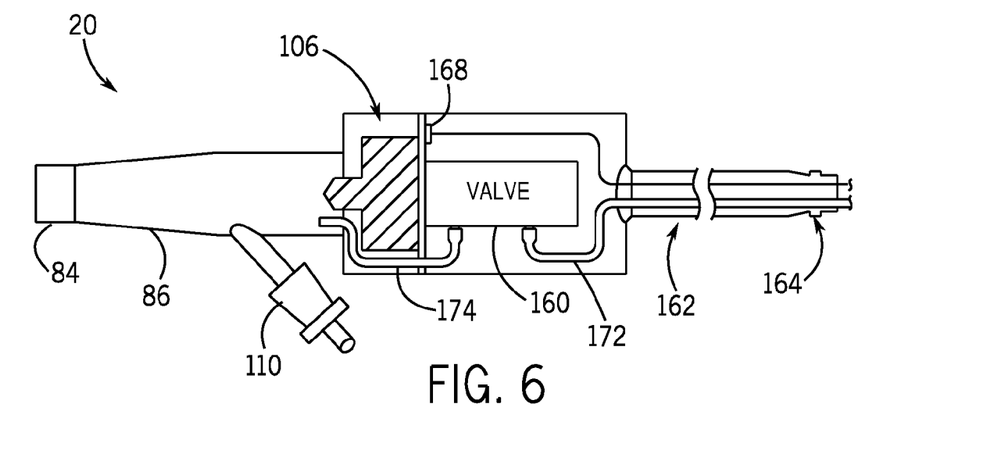
FIG. 6 is a cutaway view of an alternative arrangement of the inflation assembly of FIG. 3 along line 6-6.

The inflation assembly 20 as provided may also be implemented for closed-loop control of cuff inflation and deflation. FIG. 6 shows a cutaway view of an inflation assembly 20 that includes a valve 160 controlled by feedback from a connected medical device. In particular embodiments, the inflation assembly may also include a connector 110 for a syringe to permit manual inflation or deflation of the cuff as a bypass to closed loop control. In contrast to embodiments in which the electrical connection is mediated by a connector closed to air flow, certain embodiments of the inflation assembly may feature pneumatic tubing 162 with a hybrid connector 164 that delivers air and power at a single connection point. For example, the tubing 162 may terminate in a mini hybrid connector (Colder Products Company, St. Paul, Minn.). In one embodiment, the electrical connector portion of the hybrid connector 164 is coaxial with the fluid-carrying portion and, for example, disposed about at least part of a circumference of the fluid-carrying portion. The tubing 162 carries electrical feedback from the pressure sensor 106, which includes couplings 168 to the electrical connectors in the tubing 162 The inflation assembly 20 may use air flow via the tubing 162 to inflate or deflate the cuff. Further, to avoid deflation of the cuff upon disconnection of the connector 164 from an associated medical device, the inflation assembly 20 includes the default no-flow valve 160 that cannot open without power supplied from the connector 164. Upon disconnection of the connector 164, the valve 160 is closed and air cannot pass into the fluid passage 86 and, in turn, the inflation lumen 18.

When the connector 164 delivers power to the valve 160, the valve 160 is able to selectively open when the pressure sensor 106 provides feedback to the connected medical device with regard to low or high pressure. To provide closed loop pressure control, the inflation assembly 20 includes a fluid line 172 from the tubing 162 to allow air into and/or out of the valve 160 when the valve 160 is open. The valve 160 also includes a fluid line 174 that allows passage of air between the fluid passage 86 and the valve 160. When the valve 160 is open, air from the tubing 162 may flow through the valve 160 and into the inflation lumen 18 via fluid line 174 and fluid passage 86. Control of the valve 160 may be mediated by feedback from the pressure sensor 106 and may be under processor control by the connected medical device. For example, the monitor 30 may receive a signal from the pressure sensor 106 carried by the tubing 162 and the connector 164. In turn, based on the measured pressure, the monitor 30 provides instructions to open the valve to allow air to flow in when cuff pressure is low.

Figure 7:
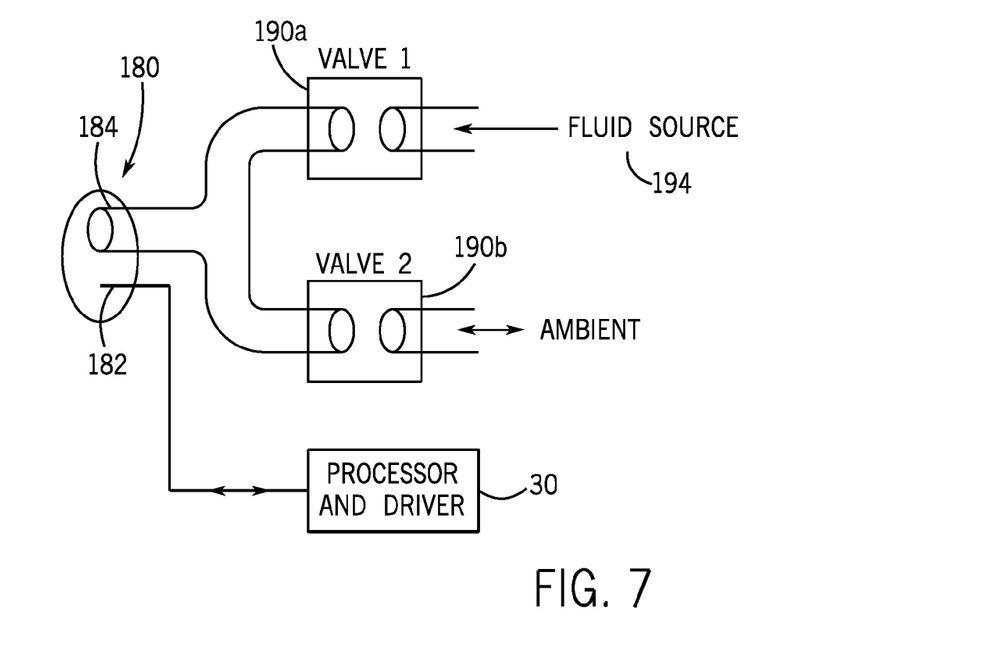
FIG. 7 is block diagram of an alternative arrangement of an inflation assembly.

The monitor 30 may also provide instructions to vent air when the cuff pressure is high. For example, as shown in FIG. 7, a pressure management system associated with the monitor 30 may include a complementary connector 180 configured to receive the hybrid connector 164 (see FIG. 6) and, accordingly, receive and carry both fluid 184 and electrical signals 182 to and from the inflation assembly 20. The system may include one or more valves 190 for controlling fluid flow. For example, a first valve 190a receives fluid from a fluid source 194 for transfer to the inflation line 18 and the cuff 14 while a second valve 190b ports fluid to ambient to lower pressure in the cuff. Both are under processor control of the monitor 30 based on feedback from the pressure sensor 106 associated with the inflation assembly 20.

In an alternative arrangement, the inflation assembly 20 may be implemented to be hot-plugged. In such an embodiment, connection of the complementary connector 180 to the hybrid connector 164 of the inflation assembly 20 causes the valve 160 in the inflation assembly 20 to open and fluid from the fluid source 194 to be transferred into the inflation cuff. Such an embodiment may be used for quick manual inflation of the cuff 14.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of cuff pressure, but these techniques may also be utilized for the measurement and/or analysis of the tracheal pressure based on measurements of cuff pressure. Rather, the various embodiments may cover all modifications, equivalents, and alternatives falling within the spirit and scope of the disclosure as defined by the following appended claims.

What is claimed is:

1. A tracheal tube system comprising:
a conduit configured to be inserted into a trachea of a subject;
an inflatable cuff disposed on the conduit and configured to contact the trachea of the subject;
an inflation line in fluid communication with the inflatable cuff, wherein the inflation line comprises an exterior portion extending away from a wall of the conduit and a distal opening disposed in an interior space of the inflatable cuff; and
an inflation assembly removably coupled to a proximal terminus of the exterior portion of the inflation line, the inflation assembly comprising:
a pressure sensor in fluid communication with the inflation line;
a lumen in selective communication with the inflation line and coupled to
a valve configured to control passage of fluids into and out of the inflation line; and
a hybrid connector disposed on a proximal terminus of the lumen and configured to carry fluid and electrical signals, wherein the valve is closed when the hybrid connector does not carry an electrical signal.

2. The tracheal tube system of claim 1, wherein the inflation assembly comprises a memory circuit storing calibration data and wherein connection of the inflation line to the inflation assembly causes a monitor to read the calibration data.

3. The tracheal tube system of claim 1, wherein the pressure sensor is electrically coupled to the hybrid connector.

4. The tracheal tube system of claim 3, wherein connection of the inflation assembly to a monitor causes the monitor to receive pressure data from the pressure sensor.

5. The tracheal tube system of claim 4, wherein the monitor is configured to deliver fluid to the inflation assembly via the hybrid connector based on the pressure data.

6. The tracheal tube system of claim 1, wherein the valve is coupled to the hybrid connector such that coupling of the hybrid connector to a power source causes the valve to open when the electrical connection is active.

7. The tracheal tube system of claim 1, wherein an electrical connector portion of the hybrid connector is disposed about at least a partial circumference of a fluid-carrying portion of the hybrid connector.

8. The tracheal tube system of claim 1, wherein uncoupling the inflation line from the inflation assembly causes the valve to close.

9. The tracheal tube system of claim 1, wherein the valve is coupled to the hybrid connector such that coupling of the hybrid connector to a power source causes the valve to open when an electrical connection is active and when a processor provides instructions to open the valve.

10. The tracheal tube system of claim 1, wherein a distal terminus of the inflation assembly comprises a Luer lock connector compatible with a complementary Luer lock connector disposed on the inflation line.

* * * * *